(12) United States Patent
Menningen et al.

(10) Patent No.: US 8,803,910 B2
(45) Date of Patent: Aug. 12, 2014

(54) SYSTEM AND METHOD OF CONTOURING A TARGET AREA

(75) Inventors: Kevin S. Menningen, Madison, WI (US); David T. Gering, Waunakee, WI (US); Kenneth J. Ruchala, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 998 days.

(21) Appl. No.: 12/549,924

(22) Filed: Aug. 28, 2009

(65) Prior Publication Data

US 2010/0053208 A1 Mar. 4, 2010

Related U.S. Application Data

(60) Provisional application No. 61/092,512, filed on Aug. 28, 2008.

(51) Int. Cl.
*G09G 5/00* (2006.01)
*G06K 9/00* (2006.01)

(52) U.S. Cl.
USPC ........... 345/626; 382/173; 382/128; 345/620; 345/624

(58) Field of Classification Search
CPC ............... G06T 7/0079; G06T 7/0089; G06T 2207/20112; G06T 2207/30; G06T 2207/30004
USPC ................... 345/626; 382/173, 131–132, 128
See application file for complete search history.

(56) References Cited

U.S. PATENT DOCUMENTS

| 4,149,081 | A |   | 4/1979  | Seppi |
|-----------|---|---|---------|-------|
| 4,998,268 | A |   | 3/1991  | Winter |
| 5,008,907 | A |   | 4/1991  | Norman et al. |
| 5,044,354 | A |   | 9/1991  | Goldhorn et al. |
| 5,065,315 | A |   | 11/1991 | Garcia |
| 5,117,829 | A | * | 6/1992  | Miller et al. .................. 600/427 |
| 5,332,908 | A |   | 7/1994  | Weidlich |
| 5,335,255 | A |   | 8/1994  | Seppi et al. |
| 5,351,280 | A |   | 9/1994  | Swerdloff et al. |
| 5,391,139 | A |   | 2/1995  | Edmundson |
| 5,394,452 | A |   | 2/1995  | Swerdloff et al. |
| 5,405,309 | A |   | 4/1995  | Carden, Jr. |
| 5,442,675 | A |   | 8/1995  | Swerdloff et al. |

(Continued)

FOREIGN PATENT DOCUMENTS

JP 10052421 2/1998
JP 10501151 2/1998

(Continued)

OTHER PUBLICATIONS

Dayton et al., "The Photoshop 5/5.5 Wow! Book", 2000, Peachpit Press, pp. 65-68, 71-75,77.*

(Continued)

*Primary Examiner* — Michelle L Sams
(74) *Attorney, Agent, or Firm* — Michael Best & Friedrich LLP (57) ABSTRACT

A two-dimensional contouring tool that allows a user to maintain a minimum distance away (in 3D) from other structures. The contouring tool allows the user to rapidly define a series of contours that conform to the shape of one or more existing contours (or targets) with user-specified margin limits between the new contour and the existing contours (or targets).

18 Claims, 6 Drawing Sheets

Step 1. Dilate the limiting area.

Step 2. Subtract result from original user-drawn contour.

(56) References Cited

U.S. PATENT DOCUMENTS

| | | | |
|---|---|---|---|
| 5,446,548 A | 8/1995 | Gerig et al. | |
| 5,471,516 A | 11/1995 | Nunan | |
| 5,511,549 A | 4/1996 | Legg et al. | |
| 5,528,650 A | 6/1996 | Swerdloff et al. | |
| 5,548,627 A | 8/1996 | Swerdloff et al. | |
| 5,552,605 A | 9/1996 | Arata | |
| 5,579,358 A | 11/1996 | Lin | |
| 5,579,409 A * | 11/1996 | Vaidyanathan et al. | 382/203 |
| 5,596,619 A | 1/1997 | Carol | |
| 5,596,653 A | 1/1997 | Kurokawa | |
| 5,621,779 A * | 4/1997 | Hughes et al. | 378/65 |
| 5,622,187 A | 4/1997 | Carol | |
| 5,625,663 A | 4/1997 | Swerdloff et al. | |
| 5,647,663 A * | 7/1997 | Holmes | 600/407 |
| 5,651,043 A | 7/1997 | Tsuyuki et al. | |
| 5,661,773 A | 8/1997 | Swerdloff et al. | |
| 5,668,371 A | 9/1997 | Deasy et al. | |
| 5,673,300 A * | 9/1997 | Reckwerdt et al. | 378/65 |
| 5,692,507 A | 12/1997 | Seppi et al. | |
| 5,712,482 A | 1/1998 | Gaiser et al. | |
| 5,724,400 A | 3/1998 | Swerdloff et al. | |
| 5,751,781 A | 5/1998 | Brown et al. | |
| 5,754,622 A | 5/1998 | Hughes | |
| 5,754,623 A | 5/1998 | Seki | |
| 5,760,395 A | 6/1998 | Johnstone | |
| 5,818,902 A | 10/1998 | Yu | |
| 5,823,192 A | 10/1998 | Kalend et al. | |
| 5,835,562 A | 11/1998 | Ramsdell et al. | |
| 6,049,587 A | 4/2000 | Leksell et al. | |
| 6,178,345 B1 | 1/2001 | Vilsmeier et al. | |
| 6,260,005 B1 | 7/2001 | Yang et al. | |
| 6,266,453 B1 | 7/2001 | Hibbard et al. | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,539,247 B2 | 3/2003 | Spetz | |
| 6,661,870 B2 | 12/2003 | Kapatoes et al. | |
| 6,735,277 B2 | 5/2004 | McNutt et al. | |
| 6,741,674 B2 | 5/2004 | Lee | |
| 6,757,355 B1 | 6/2004 | Siochi | |
| 6,792,073 B2 | 9/2004 | Deasy et al. | |
| 6,792,074 B2 | 9/2004 | Erbel et al. | |
| 6,882,702 B2 | 4/2005 | Luo | |
| 6,904,125 B2 | 6/2005 | Van Dyk et al. | |
| 6,950,544 B2 | 9/2005 | Ashton | |
| 6,961,405 B2 | 11/2005 | Scherch | |
| 7,046,762 B2 | 5/2006 | Lee | |
| 7,221,733 B1 | 5/2007 | Takai et al. | |
| 7,367,955 B2 | 5/2008 | Zhang et al. | |
| 7,450,687 B2 | 11/2008 | Yeo et al. | |
| 7,492,858 B2 | 2/2009 | Partain et al. | |
| 7,496,173 B2 | 2/2009 | Goldman et al. | |
| 7,519,150 B2 | 4/2009 | Romesberg, III et al. | |
| 7,551,717 B2 | 6/2009 | Tome et al. | |
| 7,567,694 B2 | 7/2009 | Lu et al. | |
| 7,574,251 B2 | 8/2009 | Lu et al. | |
| 7,609,809 B2 | 10/2009 | Kapatoes et al. | |
| 7,611,452 B2 | 11/2009 | Allison et al. | |
| 7,613,501 B2 | 11/2009 | Scherch | |
| 7,623,709 B2 | 11/2009 | Gering | |
| 7,639,853 B2 | 12/2009 | Olivera et al. | |
| 7,639,854 B2 | 12/2009 | Schnarr et al. | |
| 7,643,661 B2 | 1/2010 | Ruchala et al. | |
| 7,773,788 B2 | 8/2010 | Lu et al. | |
| 7,817,836 B2 | 10/2010 | Chao et al. | |
| 7,831,289 B2 | 11/2010 | Riker et al. | |
| 8,085,899 B2 | 12/2011 | Nord et al. | |
| 2002/0072671 A1 * | 6/2002 | Chenal et al. | 600/450 |
| 2003/0105650 A1 | 6/2003 | Lombardo et al. | |
| 2003/0112922 A1 | 6/2003 | Burdette et al. | |
| 2004/0068182 A1 | 4/2004 | Misra | |
| 2004/0175034 A1 * | 9/2004 | Wiemker et al. | 382/173 |
| 2005/0096515 A1 | 5/2005 | Geng | |
| 2005/0143965 A1 | 6/2005 | Failla et al. | |
| 2005/0201516 A1 * | 9/2005 | Ruchala et al. | 378/65 |
| 2005/0251029 A1 | 11/2005 | Khamene et al. | |
| 2006/0241332 A1 | 10/2006 | Klein et al. | |
| 2006/0274924 A1 * | 12/2006 | West et al. | 382/131 |
| 2006/0285639 A1 | 12/2006 | Olivera et al. | |
| 2006/0285640 A1 | 12/2006 | Nizin et al. | |
| 2006/0293583 A1 | 12/2006 | Saracen et al. | |
| 2007/0041496 A1 | 2/2007 | Olivera et al. | |
| 2007/0041498 A1 | 2/2007 | Olivera et al. | |
| 2007/0041500 A1 | 2/2007 | Olivera et al. | |
| 2007/0053490 A1 * | 3/2007 | Wang et al. | 378/65 |
| 2007/0081712 A1 | 4/2007 | Huang et al. | |
| 2007/0127790 A1 | 6/2007 | Lu et al. | |
| 2007/0197908 A1 | 8/2007 | Ruchala et al. | |
| 2008/0002809 A1 | 1/2008 | Bodduluri | |
| 2008/0002811 A1 | 1/2008 | Allison | |
| 2008/0008291 A1 | 1/2008 | Alakuijala et al. | |
| 2008/0031406 A1 | 2/2008 | Yan et al. | |
| 2008/0089479 A1 * | 4/2008 | Henkel | 378/57 |
| 2008/0193006 A1 | 8/2008 | Udupa et al. | |
| 2008/0279328 A1 | 11/2008 | Zeitler et al. | |
| 2009/0041200 A1 | 2/2009 | Lu et al. | |
| 2009/0116616 A1 | 5/2009 | Lu et al. | |
| 2009/0252291 A1 | 10/2009 | Lu et al. | |
| 2010/0054413 A1 | 3/2010 | Sobering et al. | |
| 2011/0019889 A1 | 1/2011 | Gering et al. | |

FOREIGN PATENT DOCUMENTS

| | | |
|---|---|---|
| JP | 2002210029 | 7/2002 |
| JP | 2002522129 | 7/2002 |
| JP | 2004166975 | 6/2004 |
| JP | 2005160804 | 6/2005 |
| JP | 2005518908 | 6/2005 |
| JP | 2007509644 | 4/2007 |
| JP | 2007516743 | 6/2007 |
| WO | 0007669 | 2/2000 |
| WO | 03076003 | 9/2003 |
| WO | 03092789 | 11/2003 |
| WO | 2005057463 | 6/2005 |
| WO | 2005062790 | 7/2005 |
| WO | 2007133932 | 11/2007 |

OTHER PUBLICATIONS

Purdy, James, "3D Treatment Planning and Intensity-Modulated Radiation Therapy," Oncology, vol. 13, No. 10, suppl. 5 (Oct. 1999).

Bertalmio, Marcelo, et al., "Morphing Active Contours", IEEE Transactions on Pattern Analysis and Machine Intelligence, vol. 22, No. 7, pp. 733-737, Jul. 2000.

Yu, Cedric X., et al., "A Method for Implementing Dynamic Photon Beam Intensity Modulation using Independent Jaws and a Multileaf Collimator," Phys. Med. Biol. 40. 1995: 769-787.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Lu, W., et al., "Automatic Re-Contouring Regions of Interest Based on Deformable Registration and Surface Reconstruction," AAPM 2004, (abstract: Medical Physics 31, 1845-6).

Lu, W., et al., "Automatic Re-Contouring in 4D Radiotherapy", Physical Medical Biology, 2006, Mar. 7, 51 (5):1077-99.

Lu, W., et al., 2004 "Automatic Re-Contouring for 4-D Planning and Adaptive Radiotherapy," The 90th RSNA Meeting, Chicago, Illinois, (abstract:Radiology 227 (p) 543).

Mackie, T. Rockwell et al., "Tomotherapy" Seminars in Radiation Oncology, vol. 9, No. 1, Jan. 1, 1999, pp. 108-117, XP002603992.

Rueckert, D.et al., "Nonrigid Registration Using Free-Form Deformations: Application to Breast MR Images", IEEE Transactions on Medical Imaging, vol. 18, No. 8, pp. 712-721, Aug. 1999.

PCT/US2009/055373 International Search Report and Written Opinion dated Mar. 3, 2010.

(56) References Cited

OTHER PUBLICATIONS

Mackie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," Xiith ICCR, May 27-30, 1997.

Rietzel, Eike et al., "Four-Dimensional Image-Based Treatment Planning: Target Volume Segmentation and Dose Calculation in the Presence of Respiratory Motion," International Journal of Radiation: Oncology Biology Physics, vol. 61, No. 5, pp. 1535-1550 (Apr. 1, 2005).

\* cited by examiner

Step 1. Dilate the limiting area.  Step 2. Subtract result from original user-drawn contour.

FIG. 5

Step 1. Erode the limiting area.  Step 2. Intersect eroded area with user-drawn contour.

SYSTEM AND METHOD OF CONTOURING A TARGET AREA

RELATED APPLICATIONS

This application claims priority to U.S. Provisional Patent Application No. 61/092,512, filed on Aug. 28, 2008, the entire contents of which are incorporated herein by reference.

BACKGROUND OF THE INVENTION

Radiation therapy has improved the lives of many patients who are battling cancer. Radiation therapy generally includes a series of treatments that specifically targets a cancerous tumor or other structure within the patient's body. Due to the precision required in applying the radiation to a particular area without affecting otherwise healthy tissue, radiation therapy planning software systems have been developed to better pinpoint the delivery of radiation.

In general, the current process of contouring a tumor to identify where the radiation is to be applied is mostly manually and is very time consuming. In addition, applying the contour from one image to another image requires further manual adjustments, thus dramatically increasing the time it takes to generate a treatment plan for the patient.

SUMMARY OF THE INVENTION

In general, current radiation therapy planning software systems do not allow a user to interactively draw contours around a tumor that conform to other structures. Once a contour has been drawn around the tumor, the user can manually expand or contract the contour, but the user cannot automatically limit or conform the expansion or contraction of the contour while drawing. In many cases, the user must manually etch the margin as they draw. Further, the contour can be copied into other image views but the contours would need to be manually adjusted or translated to maintain the shape and size of the margins. In addition, the copying and translation must be done slice by slice, dramatically increasing the overall time it takes to proceed with planning the treatment and making the planning process much more complex.

The present invention provides a new workflow in 2D contouring and allows the user to maintain a minimum distance away (in 3D) from other structures. More specifically, the invention provides a means by which the user can rapidly define a series of contours that conform to the shape of one or more existing contours (or targets or structures) with user-specified margin limits between the new contour and the existing contours.

In one aspect of the invention, the contouring tool allows the user to draw a contour by beginning with a fixed shape and as the user draws out that shape to conform to the target or structure on the image, the tool automatically adjusts the shape (i.e., adjusts the contour) to maintain a predetermined set of margins. The user can input one or more limits defining a perimeter or margin around a structure to prevent a contour from infringing upon the defined perimeter or margin. For example, the user can specify a perimeter of 2 mm around the heart, 3 mm around the skin, and 5 mm around the spinal cord to prevent a contour of a portion of the lung to infringe upon those perimeters. The software-based contouring tool maintains the defined set of margins in real time as the user applies the basic contour shape to the lung area. Then, the user can copy the contours onto every image slice in a different view (i.e., in a 3D image set) and the margins will be maintained during the copying process.

In one embodiment, the invention provides a method of contouring an image. The method includes acquiring an image of a patient; identifying a perimeter to be maintained from a first structure in the image; applying a contour on the image at least partially around a second structure; and limiting the contour of the second structure in substantially real-time to not infringe the perimeter of the first structure.

In another embodiment, the invention provides a method of contouring an image. The method includes displaying an image having a plurality of views of a patient on a computer screen; identifying a perimeter to be maintained from a first structure in the image; applying a contour at least partially around a second structure in one of the views of the image in a first maneuver with a computer peripheral; applying the contour to a second one of the views of the image with a second consecutive maneuver of the computer peripheral; and translating the contour onto the second one of the views of the image while limiting the contour to the second structure to not infringe the perimeter of the first structure.

In a further embodiment, the invention provides a method of contouring an image. The method includes generating a treatment plan for a patient, the treatment plan including a first image; identifying a perimeter to be maintained from a first structure in the first image; applying a contour at least partially around a second structure in the first image; acquiring a second image of the patient while in substantially a treatment position; and applying a constraint defined for the first structure from the first image to the second image when contouring the second structure in the second image.

In yet another embodiment, the invention provides a method of contouring an image. The method includes acquiring an image of a patient; applying a first contour at least partially around a first structure in the image; applying a second contour at least partially around a second structure in the image; modifying the first contour; and updating the second contour based on the modified first contour.

Other aspects of the invention will become apparent by consideration of the detailed description and accompanying drawings.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
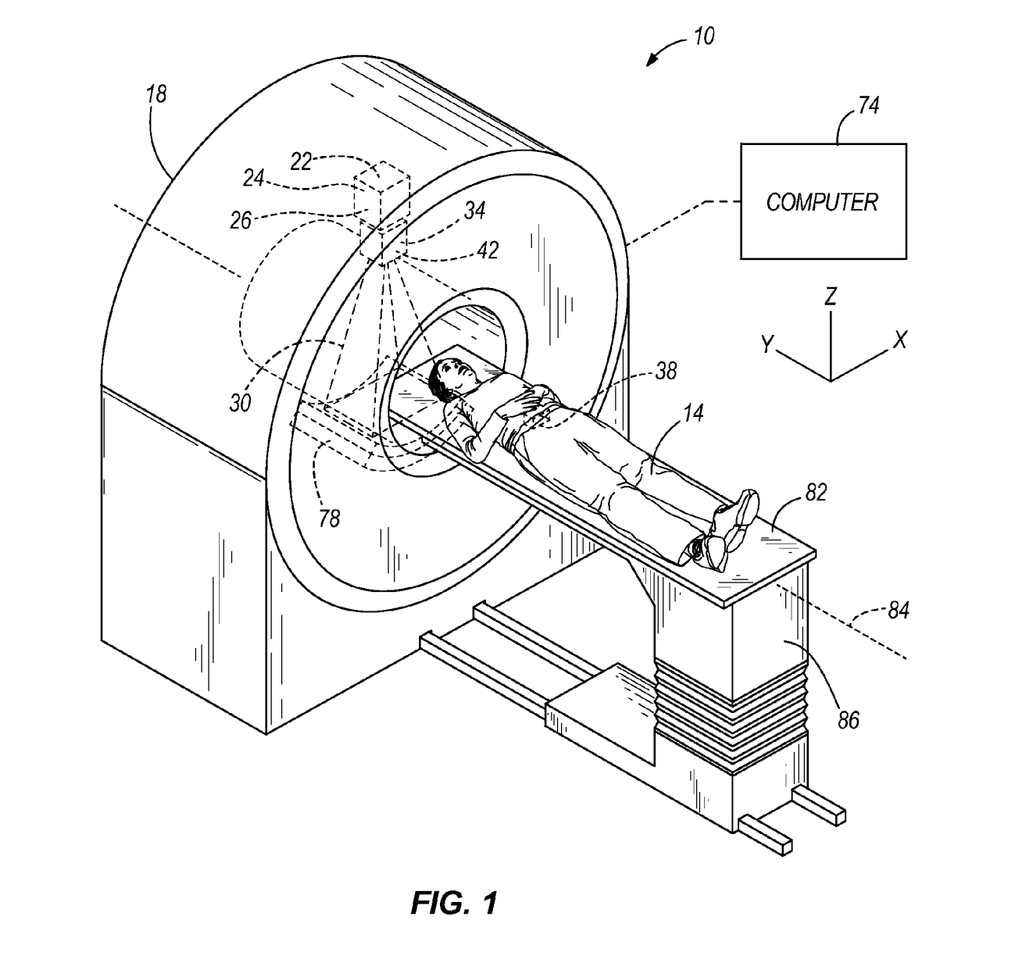
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a non-ring-shaped gantry, such as a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
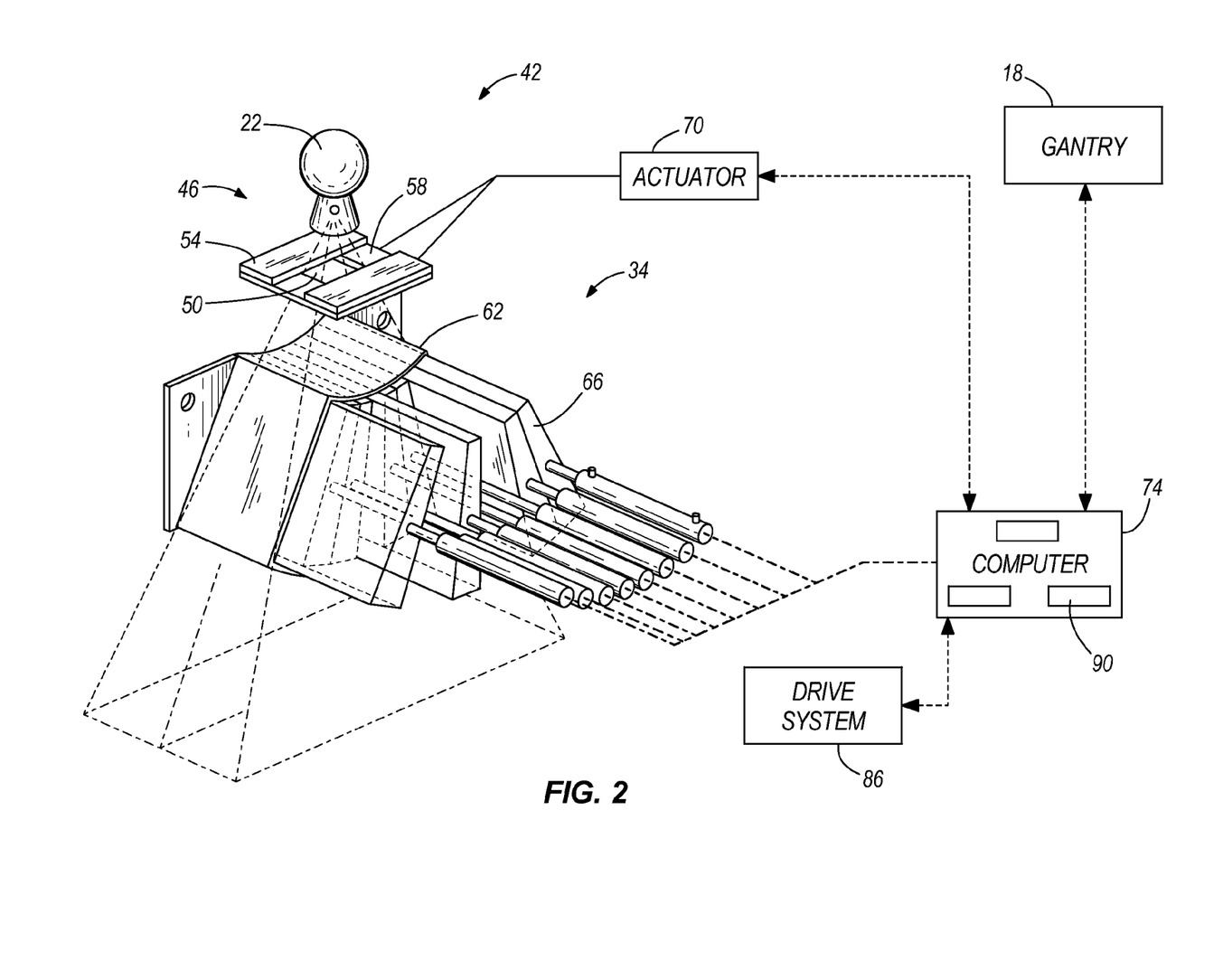
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

The image data can be presented on a video display as either a three-dimensional image or a series of two-dimensional images. In addition, the image data comprising the images can be either voxels (for three-dimensional images) or pixels (for two-dimensional images). The term image element is used generally in the description to refer to both.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
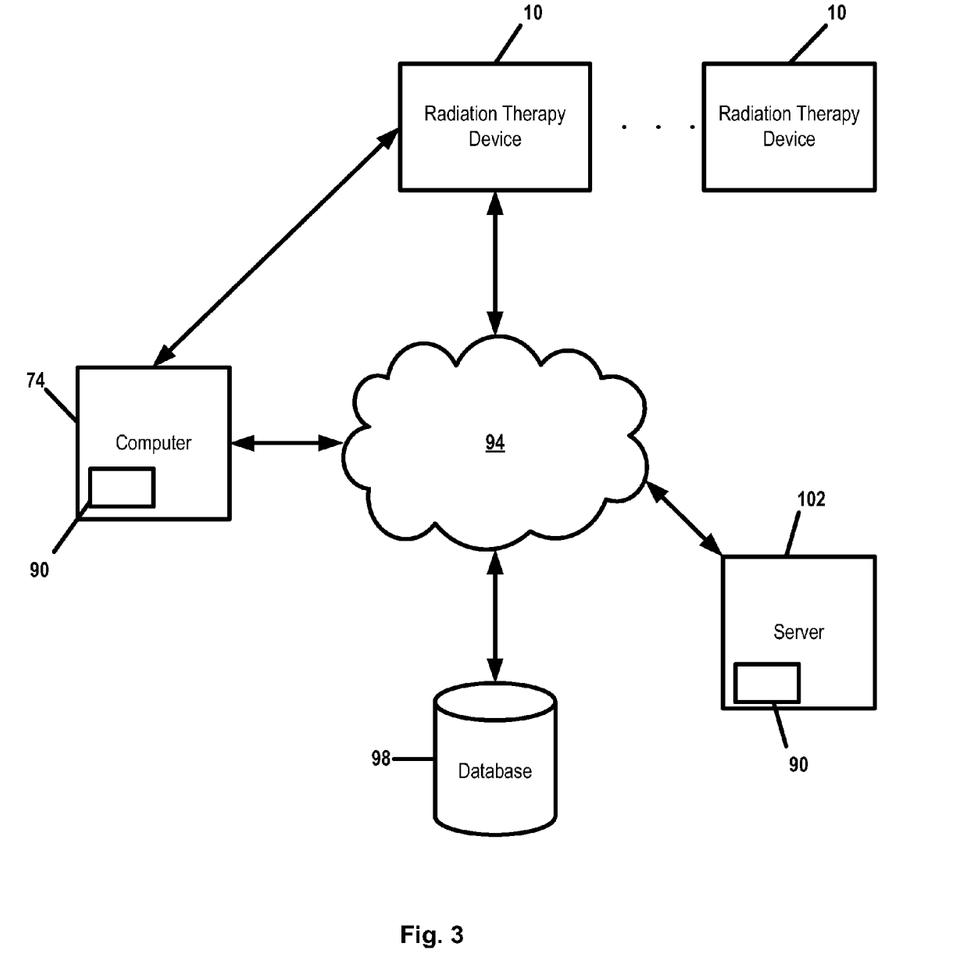
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
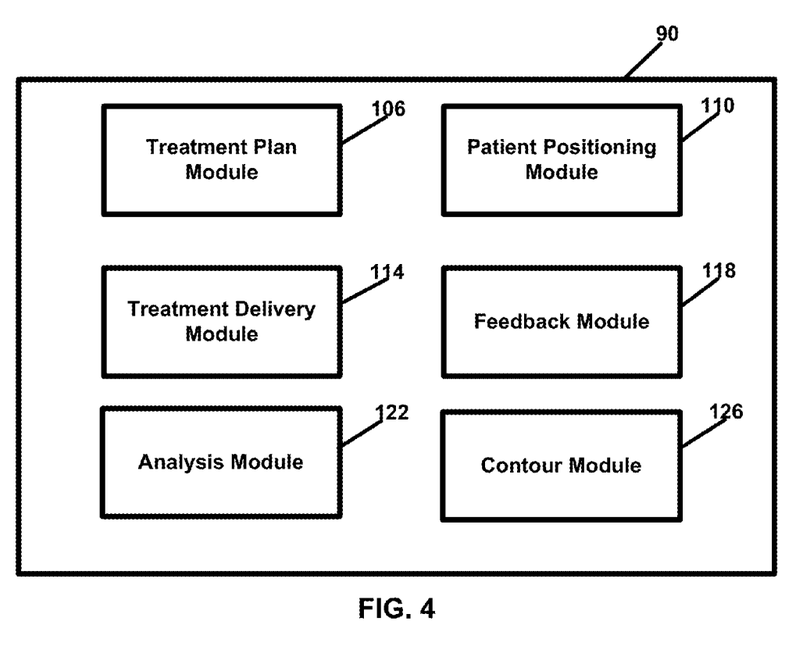
FIG. 4 is a schematic diagram of a software program used in the radiation therapy treatment system.

The software program 90 includes a plurality of modules that communicate with one another to perform functions of the radiation therapy treatment process. The various modules communication with one another to determine if delivery of the radiation therapy treatment plan occurred as intended.

The software program 90 includes a treatment plan module 106 operable to generate a treatment plan for the patient 14 based on data input to the system 10 by medical personnel. The data can include one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes a patient positioning module 110 operable to position and align the patient 14 with respect to the isocenter of the gantry 18 for a particular treatment fraction. While the patient is on the couch 82 and prior to delivery of the treatment plan, the patient positioning module 110 acquires an image of the patient 14. The patient positioning module 110 can include an image module that can instruct an on-board image device, such as a CT imaging device to acquire one or more pre-treatment images of the patient 14 before treatment commences. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired pre-treatment image(s) can be used for registration of the patient 14 and/or to generate a deformation map to identify the differences between one or more of the planning images and one or more of the pre-treatment images.

For positioning purposes, the patient positioning module 110 can compare the current position of the patient 14 in a pre-treatment image to the position of the patient in a reference or planning image. The reference image can be a planning image, any pre-treatment image, or a combination of a planning image and a pre-treatment image. If the patient's position needs to be adjusted, the patient positioning module 110 provides instructions to the drive system 86 to move the couch 82 or the patient 14 can be manually moved to the new position. In one construction, the patient positioning module 110 can receive data from lasers positioned in the treatment room to provide patient position data with respect to the isocenter of the gantry 18. Based on the data from the lasers, the patient positioning module 110 provides instructions to the drive system 86, which moves the couch 82 to achieve proper alignment of the patient 14 with respect to the gantry 18. It is noted that devices and systems, other than lasers, can be used to provide data to the patient positioning module 110 to assist in the alignment process.

The patient positioning module 110 also is operable to detect and/or monitor patient motion during treatment. The patient positioning module 110 may communicate with and/or incorporate a motion detection system 112, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes a treatment delivery module 114 operable to instruct the radiation therapy treatment system 10 to deliver the treatment plan to the patient 14 according to the treatment plan. The treatment delivery module 114 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 according to a fluence map to deliver the radiation beam 30 to the proper target in the proper amount as specified in the treatment plan.

The treatment delivery module 114 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 114 can utilize canonical, predetermined or template leaf patterns to generate the appropriate pattern for the radiation beam 30 based on the treatment parameters. The treatment delivery module 114 can also include a library of patterns for typical cases that can be accessed in which to compare the present patient data to determine the pattern for the radiation beam 30.

The software program 90 also includes a feedback module 118 operable to receive data from the radiation therapy treatment system 10 during a patient treatment. The feedback module 118 can receive data from the radiation therapy treatment device and can include information related to patient transmission data, ion chamber data, fluence output data, MLC data, system temperatures, component speeds and/or positions, flow rates, etc. The feedback module 118 can also receive data related to the treatment parameters, amount of radiation dose the patient received, image data acquired during the treatment, and patient movement. In addition, the feedback module 118 can receive input data from a user and/or other sources. The feedback module 118 acquires and stores the data until needed for further processing.

The software program 90 also includes an analysis module 122 operable to analyze the data from the feedback module 118 to determine whether delivery of the treatment plan occurred as intended and to validate that the planned delivery is reasonable based on the newly-acquired data. The analysis module 122 can also determine, based on the received data and/or additional inputted data, whether a problem has occurred during delivery of the treatment plan. For example, the analysis module 122 can determine if the problem is related to an error of the radiation therapy treatment device 10, an anatomical error, such as patient movement, and/or a clinical error, such as a data input error.

The analysis module 122 can detect errors in the radiation therapy treatment device 10 related to the couch 82, the device output, the gantry 18, the multi-leaf collimator 62, the patient setup, and timing errors between the components of the radiation therapy treatment device 10. For example, the analysis module 122 can determine if a couch replacement was performed during planning, if fixation devices were properly used and accounted for during planning, if position and speed is correct during treatment.

The analysis module 122 can determine whether changes or variations occurred in the output parameters of the radiation therapy treatment device 10. With respect to the gantry 18, the analysis module 122 can determine if there are errors in the speed and positioning of the gantry 18. The analysis module 122 can receive data to determine if the multi-leaf collimator 62 is operating properly. For example, the analysis module 122 can determine if the leaves 66 move at the correct times, if any leaves 66 are stuck in place, if leaf timing is properly calibrated, and whether the leaf modulation pattern is correct for any given treatment plan. The analysis module 122 also can validate patient setup, orientation, and position for any given treatment plan. The analysis module 122 also can validate that the timing between the gantry 18, the couch 62, the linear accelerator 26, the leaves 66 are correct.

The software program 90 can also include a contour module 126 operable to generate one or more contours on a two-dimensional or three-dimensional image. Medical personnel can manually define a contour around a target 38 on one of the patient images. The contour module 126 receives input from a user that defines a margin limit to maintain from other contours or objects. The contour module 126 includes a library of shapes (e.g., rectangle, ellipse, circle, semi-circle, half-moon, square, etc.) from which a user can select to use as a particular contour. The user also can select from a free-hand option. The contour module 126 allows a user to drag a mouse (a first mouse dragging movement or swoop) or other suitable computer peripheral (e.g., stylus, touchscreen, etc.) to create the shape on a transverse view of an image set. An image set can include a plurality of images representing various views such as a transverse view, a coronal view, and a sagittal view. The contour module 126 can automatically adjust the contour shape to maintain the user-specified margins, in three dimensions, and can then display the resulting shape. The center point of the shape can be used as an anchor point. The contour module 126 also allows the user to drag the mouse a second time (a second consecutive mouse dragging movement or swoop) onto a coronal or sagittal view of the image set to create an "anchor path." The same basic contour shape is copied or translated onto the corresponding transverse views, and can be automatically adjusted to accommodate the user-specified margins on each view independently. The shape is moved on each view so that the new shape's anchor point is centered on a point corresponding to the anchor path in the coronal and sagittal views. The contour module 126 allows the user to make adjustments to the shapes on each slice. The user may also make adjustments to the limits they specified and the contour module 126 updates the shapes accordingly. Additionally, the user can adjust the anchor path to move individual slice contours accordingly. The contour module 126 provides an option for the user to accept the contour set, and if accepted, the shapes are converted into normal contours for editing.

With only two mouse movements (two swoops), the contour module 126 provides the user the ability to create a large number of independent contour shapes, all or substantially all of them conforming to other structures in three dimensions according to the limits specified.

As an example, the contour module 126 can be used to contour the spinal cord. To do this, a circle tool is selected and limits are entered for other structures (such as 2 mm from the skin). The user first draws the circle on one view of the current image slice so that it envelops the spinal cord. The system adjusts the circle shape as necessary to avoid infringing upon the 2 mm limit from the skin. Then the user draws a path from a transverse view of the current image slice to a sagittal or coronal view of the current image slice to apply the contour to the spine. The user also can apply the contour to multiple image slices to follow the S-shaped curve of the spine. The user draws a path from the current image slice to any number of additional slices to apply the contour to the spine while maintaining the 2 mm limit for the skin. For each slice except the original slice that has been drawn upon, the contour module 126 copies the circle shape, centers the copy upon the path drawn, and then adjusts the shape so that it maintains the 2 mm limit from the skin.

In another example, the contour module 126 can be used to contour a breast. The user enters in some limits such as 15 mm from the heart, 5 mm from the skin, and −2 mm from the lung. The user selects a half-circle shape and draws a contour in the transverse view so that the flat part of the half-circle follows the imaginary baseline of the breast tissue. The contour module 126 then adjusts the half-circle shape so that it remains 15 mm from the heart, 5 mm from the skin, and allows it to overlap the lung by as much as 2 mm but no more. The user then selects an anchor point on the sagittal view of the current slice and draws a path or link from the sagittal view of the current slice to other slices to apply the contour onto the other slices in the image set covering the breast. Each contour copy is moved to follow the path and is then adjusted so that it meets the 15 mm, 5 mm, and −2 mm limits in the other slices.

During the course of treatment, the patient typically receives a plurality of fractions of radiation (i.e., the treatment plan specifies the number of fractions to irradiate the tumor). For each fraction, the patient is registered with respect to the radiation delivery device. After the patient is registered, a daily pre-treatment image (e.g., a 3D or volumetric image) is acquired while the patient remains in substantially a treatment position. The pre-treatment image can be compared to previously acquired images of the patient to identify any changes in the target 38 or other structures over the course of treatment. The changes in the target 38 or other structures is referred to as deformation. Deformation may required that the original treatment plan be modified to account for the deformation. Instead of having to recontour the target 38 or the other structures, the contour module 126 can automatically apply and conform the preexisting contours to take into account the deformation. To do this, a deformation algorithm identifies the changes to the target 38 or other structures. These identified changes are input to the contour module 126, which then modifies the contours based on those changes.

A contour can provide a boundary for autosegmenting the structure defined by the contour. Segmentation is the process of assigning a label to each voxel. The label represents the type of tissue present. It is stored as an image (array of voxels). The finalization of the contour can trigger an algorithm to automatically segment the tissue present within the boundaries of the contour.

As noted above, the user can elect to use an anchor path. An anchor point is specified on the slice the contour is being drawn upon. The Ganged TCS cursor is used to depict the anchor point. The anchor point can be centered upon the source contour on the slice the source contour resides upon. The user can specify that any point on the slice is the anchor point. If the user moves the slice using the vertical Ganged TCS cursor in the sagittal or coronal views, the source contour is moved to the new slice.

The first time the user draws a path on the sagittal or coronal views, the anchor path is created. For each slice (horizontal voxel in the sagittal or coronal view), a copy of the source contour is made on that slice and conformed to the limiting structures. While drawing the anchor path, as the line traverses the slice upon which the source contour is on, the anchor point is used instead of the mouse point. For example, if the user sets the anchor point 5 mm below the skin, but then draws the anchor line such that the line intersects with the source contour slice at 10 mm below the skin, the source contour is not moved. Instead, the anchor path is made to connect with the point at 5 mm below the skin.

Once the anchor path is drawn, the user may modify it to automatically move/translate the contour on those slices to be centered upon the anchor path point. When the anchor path is specified, the source contour is copied to each slice that is traversed by the anchor path. Each contour copy is centered upon the point at which the anchor path intersects the slice plane.

If the user moves the Ganged TCS cursor for position in the PVCS XY plane after the anchor path is drawn, the movement simply modifies that point on the anchor path that intersects the slice for the source contour, and therefore translates the source contour accordingly. If the user moves the Ganged TCS cursor for the PVCS Z plane (slice) after the anchor path is defined, the entire anchor path is moved. This allows the user to "nudge" the entire set of curves a few slices inferior or superior to where they started.

The contour module 126 includes an algorithm that allows the user to specify a minimum distance from a particular structure called the limiting structure. The objective of the algorithm is to construct an area such that the minimum distance is maintained. In this discussion, the current area being drawn by the user, and which must conform to the limits, is referred to as C. The area represented by the limiting structure, referred to as L, becomes either the outside limit or the inside limit for the contour being drawn. Each limiting structure is handled separately and the effects accumulated. For example, if the user wishes to remain 5 mm from the skin structure and 15 mm from the heart, the limiting area for the skin is calculated separately from the heart, but both are added together in order to calculate the proper effect on the new contour.

There are two broad cases to consider, an outside limit or an inside limit. These are decided by where the initial mouse-Pressed( ) event is received. If the mouse point is inside L, then the structure forms an outside limit beyond which the new contour cannot grow. If the mouse point is outside L, then the structure forms an inside limit, and if the new contour completely envelopes it, a hole is formed in the new contour. Whether L forms an inside or outside limit can be determined using the Java2D Area.contains( ) method.

Figure 5:
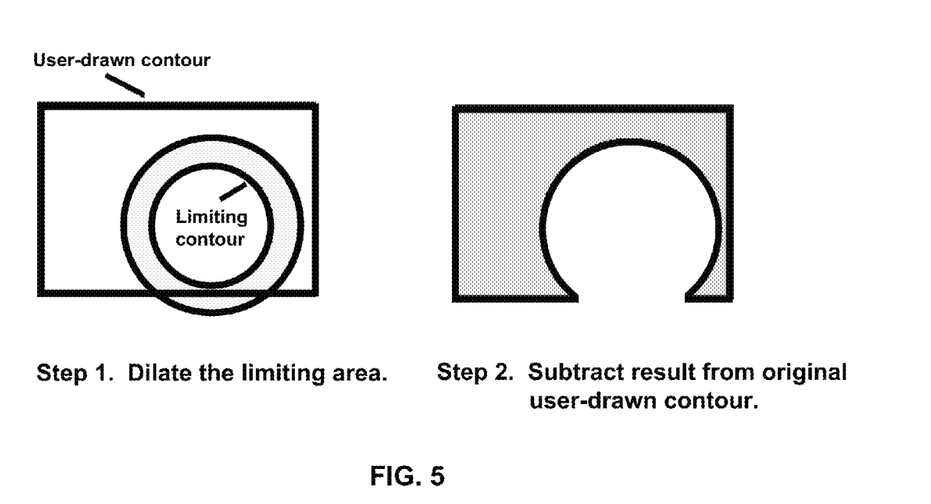
FIG. 5 illustrates a process of calculating an inside limit.

For an inside limit (mouse press outside the limiting structure), the algorithm is straightforward for the limiting structure's contours on the plane the user is drawing on. L is dilated by the user-specified margin using the Uniform Margin algorithm, and then the dilated area is subtracted from C to form the resulting area R. The equation for an inside limit is therefore:

$$R_{inside} = C - L$$

The subtraction is accomplished using Java2D Area.subtract( ). FIG. 5 illustrates this process. Handling contours for the limiting structure on other nearby slices is treated separately below.

Figure 6:
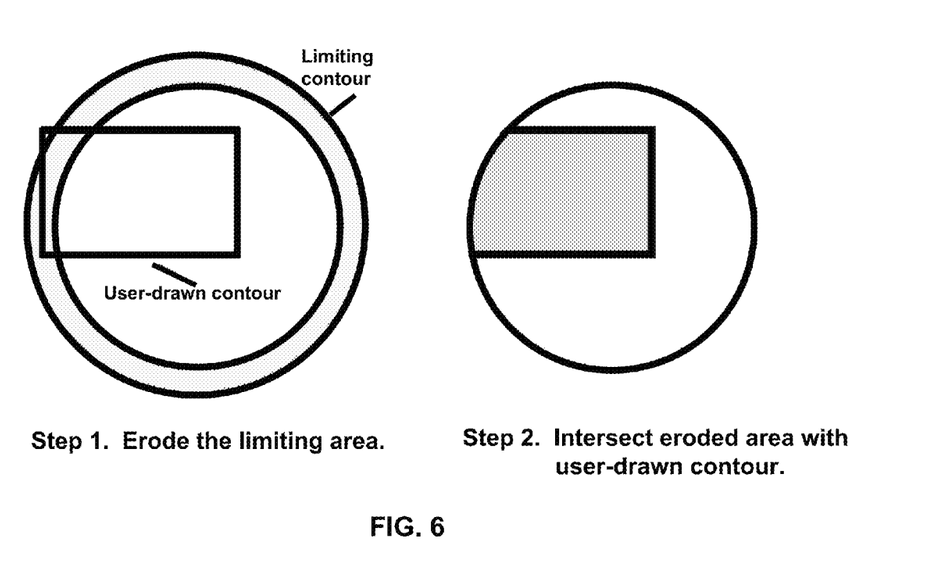
FIG. 6 illustrates a process of calculating an outside limit.

For an outside limit (mouse press inside the limiting structure) the algorithm for using the limiting structure's contours on the plane the user is drawing on is a bit different. We first erode L by the user-specified margin using the Uniform Margin code. Then we take the intersection of the eroded L with C to form the resulting area R. The equation for an outside limit is therefore:

$$R_{outside} = C \cap L$$

This process for handling outside limits is illustrated graphically in FIG. 6. The subtractions are accomplished using Java2D Area.intersect( ). Handling contours for the limiting structure on other nearby slices is treated separately below.

Contours for limiting structures can also be used on slices next to the slice that C is on to maintain three dimensional distances from the limiting structure. This works for both inside and outside limits, and is a fast alternative to performing the calculations in 3D. The algorithm is based upon modeling a sphere of the user-specified radius around each point on the curves on a neighboring slice. These spheres intersect with the slice the user is currently working on. If you connect these spheres together, they form the very same shape as the curve on the neighboring slice, and the shape is either eroded or dilated. The erosion or dilation of the shape is by a smaller amount than if the limiting curve was on the current slice. If the neighboring curve forms an outside limit, the shape is eroded. If it forms an inside limit, the shape is dilated. The eroded or dilated shape is projected onto the current slice and used as a limiting structure.

For all of the neighboring slices that are within limits, the eroded or dilated areas are added together to form a union area. This union area does not need to be recalculated unless the slice is changed, so once it is calculated it can be used with Java2D to rapidly determine the shape of the user's contour.

Figure 7:
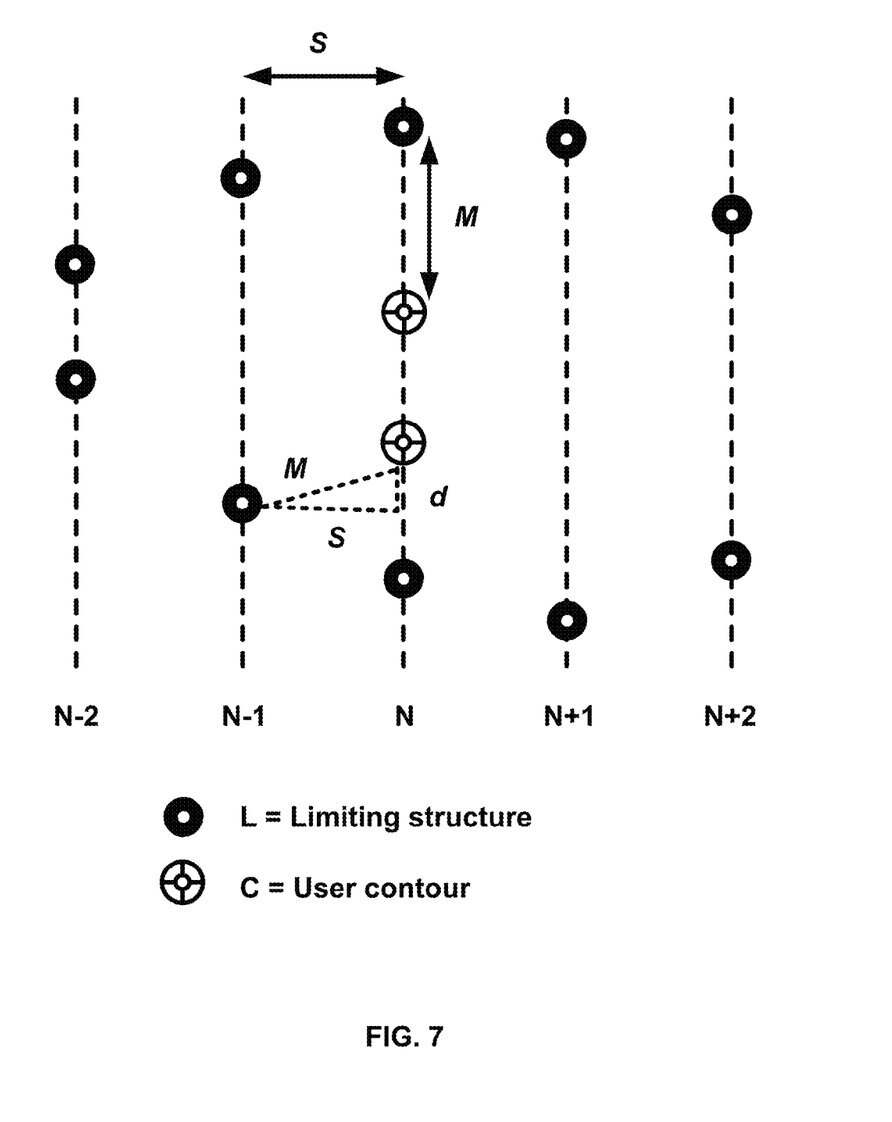
FIG. 7 illustrates a process of determining the amount by which to erode or dilate contours on neighboring slices.

The objective of the neighboring slices calculation is to determine the amount by which to erode or dilate a projection of L for the neighboring slice onto the slice C is on. The amount by which it is eroded or dilated can be calculated as:

$$d_i = \sqrt{m^2 - s_i^2}$$

where $d_i$ is the distance to dilate or erode, m is the minimum distance from the limiting structure as defined by the user, and $s_i$ is the total slice thickness from the $i^{th}$ neighboring slice to the slice the user is working on. When on the current slice, s is zero and therefore d=m. As s increases due to moving one or more slices away, d will become less than m. This equation will not work if s is greater than m, so only those slices that are less than m centimeters away from the working slice can be included. This makes sense because contours on slices farther away than m will not influence the current slice in any way. A conservative approach might still round up one slice beyond this point, and simply use zero for d, keeping the user's contour away from the structure without dilating or eroding, as if the slice were exactly m centimeters away.

The equation's derivation may be easier to understand by reviewing FIG. 7, which shows a series of contours from a sagittal or coronal view. FIG. 7 illustrates a sagittal view of patient image slices, with the intersection of the curves for two contours shown as dots. In this diagram we're dealing with an outside limit, because the C is inside L. On current slice N, L must be eroded by distance m so that the user contour is kept at least m centimeters away from L. For neighboring slice N-1, the contour must be eroded by a smaller amount prior to limiting the user's contour. This smaller amount d can be calculated by Pythagorean's Theorem on the triangle indicated. A similar argument is made that inside limits from neighboring slices must be dilated by d.

The union area of the current slice's result R and the neighboring slice's R is used as the limiting area per the algorithm described above. The decision about whether the limiting contour is an inside or an outside limit is based solely upon where the user clicks on the current slice. If there are no contours for the limiting structure on the current slice, then an outside limit is assumed (because the current slice is outside of the limiting structure).

Various features and advantages of the invention are set forth in the following claims.

What is claimed is:

1. A method of contouring an image, the method comprising:
   acquiring an image of a patient;
   generating, at a processor, a first contour around a sensitive structure in the image;
   defining, at a processor, a distance to be maintained from the first contour in the image;
   defining a perimeter at least partially around the sensitive structure based on the distance; and
   applying, at a processor, a second contour on the image at least partially around a target structure for receiving radiation while limiting the second contour of the target structure in substantially real-time to not infringe the perimeter of the sensitive structure.

2. The method of claim 1 wherein the image is three-dimensional.

3. The method of claim 1 wherein applying the second contour includes simultaneously generating a constrained contour.

4. The method of claim 1 wherein applying the second contour on the image includes avoiding certain pre-defined structures in the image.

5. The method of claim 1 wherein the second contour is applied to the image based on a protocol.

6. The method of claim 1 wherein the target structure is autosegmented based on the second contour.

7. A method of contouring an image, the method comprising:
   generating, at a processor, a treatment plan for a patient, the treatment plan including a first image;
   generating, at a processor, a first contour around a sensitive structure in the first image;
   defining, at a processor, a distance to be maintained from the first contour in the first image;
   defining a perimeter at least partially around the sensitive structure based on the distance;
   applying, at a processor, a second contour at least partially around a target structure in the first image;
   acquiring, at a processor, a second image of the patient while in substantially a treatment position; and
   applying, at a processor, a constraint defined for the sensitive structure from the first image to the second image when contouring the target structure in the second image.

8. The method of claim 7 further comprising selecting, at a processor, a shape for one of the first contour and the second contour, applying, at a processor, an anchor point on the first image, and storing the shape and the anchor point.

9. The method of claim 8 wherein contouring the target structure in the second image includes retrieving the stored shape and the anchor point and applying the stored shape and the anchor point to the target structure.

10. The method of claim 7 wherein the second image includes deformation to the target structure and wherein the contour of the target structure in the second image automatically adjusts for the deformation.

11. The method of claim 10 further comprising automatically applying, at a processor, a contour to the sensitive structure in the second image.

12. The method of claim 7 wherein the second contour is applied to the first image based on a protocol and wherein contouring the second image includes using the protocol.

13. The method of claim 7 wherein the constraint is the perimeter of the sensitive structure.

14. The method of claim 7 further comprising comparing, at a processor, the first image and the second image to identify differences in the sensitive structure, and wherein the perimeter of the sensitive structure is modified to accommodate the differences, and wherein the constraint is the modified perimeter of the sensitive structure.

15. The method of claim 7 wherein the first image and the second image are three-dimensional.

16. The method of claim 7 wherein applying the second contour includes simultaneously generating a constrained contour.

17. The method of claim 7 wherein applying the second contour on the first image and the contour on the second image includes avoiding certain pre-defined structures in the images.

18. The method of claim 7 wherein the target structure is autosegmented based on the second contour.

* * * * *